United States Patent [19]

Negawa et al.

[11] Patent Number: 5,498,752

[45] Date of Patent: Mar. 12, 1996

[54] PROCESS FOR RECOVERING OPTICAL ISOMERS AND SOLVENT, PROCESS FOR USING SOLVENT BY CIRCULATION AND PROCESS FOR REUSING OPTICAL ISOMERS IN OPTICAL RESOLUTION

[75] Inventors: Masakazu Negawa; Fumihiko Shoji, both of Hyogo, Japan

[73] Assignee: Daicel Chemical Industries, Ltd., Osaka, Japan

[21] Appl. No.: 202,970

[22] Filed: Feb. 28, 1994

Related U.S. Application Data

[60] Continuation-in-part of Ser. No. 156,264, Nov. 22, 1993, Pat. No. 5,434,299, which is a division of Ser. No. 30,063, Mar. 12, 1993, Pat. No. 5,434,298.

[30] Foreign Application Priority Data

Aug. 22, 1991 [JP] Japan ................................ 3-210565

[51] Int. Cl.$^6$ ................................................ B01D 15/08
[52] U.S. Cl. ...................... 560/249; 210/198.2; 210/659; 562/608
[58] Field of Search .............................. 210/659, 198.2; 560/34, 249; 562/249, 608

[56] References Cited

U.S. PATENT DOCUMENTS

| | | | |
|---|---|---|---|
| 2,985,589 | 5/1961 | Broughton et al. | 210/34 |
| 4,842,935 | 6/1989 | Shinbo et al. | 428/404 |
| 5,032,277 | 7/1991 | Okamoto et al. | 210/635 |
| 5,126,055 | 6/1992 | Yamashita et al. | 210/659 |
| 5,135,653 | 8/1992 | Okamoto et al. | 210/635 |

FOREIGN PATENT DOCUMENTS 2593409 7/1987 France .

OTHER PUBLICATIONS

*UOP Sorbex Processes*, Nikki Universal Co., Ltd., Oct., 1989.

*Primary Examiner*—Arthur C. Prescott
*Attorney, Agent, or Firm*—Flynn, Thiel, Boutell & Tanis

[57] ABSTRACT

A process for recovering and reusing a solvent and optical isomers, characterized by using a simulated moving packed bed which comprises an inlet for an eluent, an outlet for an extract containing an optical isomer strongly adsorbable on the packing, an inlet for a liquid containing an optical isomer mixture and an outlet for a raffinate containing an optical isomer weakly adsorbable on the packing in this order in a packed bed containing packings for optical resolution and arranged in a solvent circulation passage, and in which the inlets and the outlets are intermittently and successively moved in the direction of liquid flow in the packed bed: recovering the solvent and the optical isomer(s) from The resultant extract and/or raffinate; returning the recovered solvent into the solvent circulation passage; or when the solvent is not recovered, heating the extract or raffinate to racemize an undesired optical isomer and reusing the resultant solution containing a racemic modification for the separation of the optical isomers with the simulated moving bed system.

12 Claims, 2 Drawing Sheets

PROCESS FOR RECOVERING OPTICAL ISOMERS AND SOLVENT, PROCESS FOR USING SOLVENT BY CIRCULATION AND PROCESS FOR REUSING OPTICAL ISOMERS IN OPTICAL RESOLUTION

This is a continuation-in-part of Ser. No. 08/156,264, filed Nov. 22, 1993, now U.S. Pat. No. 5,434,299 which is a division of Ser. No. 08/030,063, filed Mar. 12, 1993, now U.S. Pat. No. 5,434,298.

FIELD OF INDUSTRIAL APPLICATION

The present invention relates to a process for recovering optical isomers and a solvent, a process for using the solvent by circulation and a process for reusing the optical isomers. In particular, the present invention relates to a process for recovering optical isomers and a solvent, wherein the optical isomers can be efficiently separated from each other and the solvent used for the optical resolution can be efficiently recovered, a process for using the solvent by circulation, wherein the solvent recovered by the recovering process of the present invention is reused for the effective utilization of the solvent, and a process for reusing the optical isomers, wherein the intended optical isomers obtained by the optical resolution are reused without being discarded so as to further improve the efficiency of the optical resolution.

PRIOR ART

It is well known that optical isomers have different effects on the living body, though they are chemically the same. Therefore, it is an extremely important problem in the industrial fields of medicines, pharmacy, biochemistry, etc., to prepare an optically pure compound in order to improve the efficacy of the medicine per unit quantity and to prevent drug-induced sufferings caused by adverse reactions of the drug. For the separation of such an optical isomer mixture, i.e., optical resolution of them, a diastereomer method, crystallization method, enzyme method, separating membrane method or the like has been employed heretofore. However, such a method is generally unsuitable, since the kinds of the compounds which can be optically resolved are usually limited. Although chromatography can be employed for the optical resolution, the chromatographic methods known at present are of a batch type and hence cannot avoid discontinuous and unstationary operations, which is unsuitable for the mass processing. Further this chromatographic method has another defect that since a large amount of an eluent is necessitated and the concentration of the intended compound in the eluate is low, much energy and complicated steps are necessitated for the recovery.

An object of the present invention is to provide a novel process which can separate optical isomers and a solvent efficiently from a large amount of a mixture comprising the optical isomers. Another object of the present invention is to provide a process for efficiently separating each of optical isomers and a solvent from a large amount of a mixture comprising the optical isomers and also reusing the recovered solvent.

DISCLOSURE OF THE INVENTION

The invention which solves the above problem relates To a process for recovering optical isomers and a solvent in optical resolution by introducing a liquid containing an optical isomer mixture and an eluent into a packed bed containing packings for optical resolution, having both ends connected to each other through a fluid passage to be endless and circulating the liquids therein by one-way flow, and simultaneously recovering a liquid containing one optical isomer and a liquid containing the other optical isomer which are separated from the packed bed, characterized by arranging an inlet for the eluent, an outlet for a liquid (extract) containing an easily adsorbable optical isomer, an inlet for the liquid containing an optical isomer mixture, and an outlet for a liquid (raffinate) containing a difficultly adsorbable optical isomer in this order in the direction of liquid flow onto the packed bed, and recovering the solvent and optical isomers from the extract and/or raffinate thus obtained with a simulated moving bed system that the inlets and the outlets are intermittently and successively moved in the direction of liquid flow in the bed.

Further, the invention relates to the above mentioned process for recovering optical isomers and a solvent, wherein the packing for optical resolution has a particle diameter of 1 to 100 μm, the invention relates to the above mentioned process for recovering optical isomers and a solvent in optical resolution, wherein the solvent is separated from the extract and/or raffinate obtained with the simulated moving bed system with an evaporator and/or a still, the invention relates to the above mentioned process for recovering optical isomers and a solvent in optical resolution, wherein the above evaporator and/or still is of reduced pressure type, the invention relates to a process for using a solvent by circulation, characterized by returning the solvent recovered by the above mentioned process into the fluid passage, the invention relates to the above mentioned process for using a solvent by circulation, wherein the recovered solvent has a purity of at least and, the invention relates to a process for reusing an optical isomer, wherein the optical isomer as an antipode in the above mentioned extract or raffinate is racemized and the resultant liquid containing an optical isomer mixture is returned into an inlet for a liquid containing an optical isomer mixture.

Figure 1:
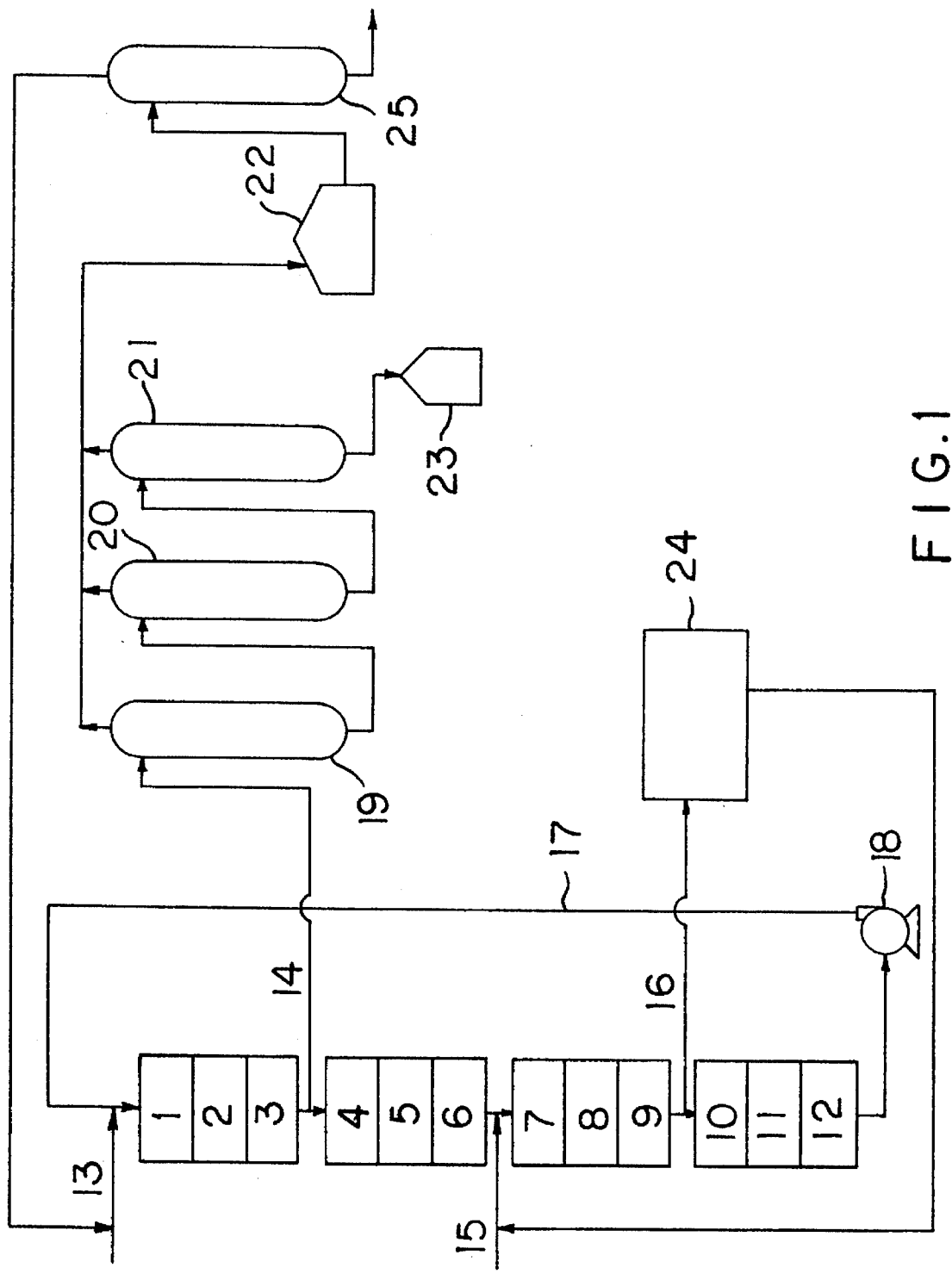
FIG. 1 is a drawing for illustrating one example of the apparatuses usable for conducting the process of the present invention.

1 to 12: unit packed bed
13: line for feeding eluent
14: line for ejecting extract
15: line for feeding liquid containing optical isomer mixture
16: line for ejecting raffinate
17: recycle line
18: circulation pump
19: first falling film evaporator
20: second falling film evaporator
21: forced film evaporator
22: recovery tank
23: reservoir 24: racemization tank
25: still The present invention will be described in detail in the following.

A. Simulated moving bed:

In the simulated moving bed system, use is made of, for example, a simulated moving bed as shown in FIG. 1 which is divided into a plurality of (for example, 12 or 8) unit packed beds arranged in series in the liquid passage in which liquid is circulated. The liquid is unidirectionally circulated in The liquid passage. The number of the unit packed beds in the simulated moving bed is not limited to those described above, but can be suitably selected depending on the scale and from the viewpoint of reaction engineering.

The simulated moving bed has an inlet for an eluent, an outlet for ejecting a liquid (extract) containing an optical isomer strongly adsorbable on the packing, an inlet for a liquid containing an optical isomer mixture, and an outlet for ejecting a liquid (raffinate) containing an optical isomer weakly absorbable on the packing in this order in the direction of liquid flow, and they can be intermittently and successively moved in the direction of liquid flow in the packed bed.

The simulated moving bed system per se is well known as described in, for example, Japanese Patent Publication-B No. 15881/1987. However, the simulated moving bed system has heretofore been employed only for the production of fructose, separation of maltose and recovery of co-enzymes and no process has been described at all for separating optical isomers by this system.

In the simulated moving bed system shown in FIG. 1, an inlet for an eluent, an outlet for an extract, an inlet for a liquid containing an optical isomer mixture and an outlet for a raffinate are provided for every three unit packed beds. These inlets and outlets are intermittently and successively moved by means of, for example, rotary valves.

Kind of Packings for Optical Resolution and the Like

Each unit packed bed contains packings having an optical resolving ability. The packings include those for optical resolution made of an optically active polymeric compound and a low-molecular compound having an optical resolving ability. Examples of the optically active polymeric compounds include polysaccharide derivatives (such as esters and carbamates of cellulose and amylose), polyacrylate derivatives, packings comprising a polyamide derivative carried by silica gel, and packings prepared by granulating the polymer per se without using any silica gel. Examples of the low-molecular compounds having an optical resolving ability include crown ethers and derivatives Thereof and cyclodextrin and derivatives thereof. These low-molecular compounds are usually employed by being supported on a support such as silica gel.

Commercially available packings for optical resolution are also usable. Examples of preferred ones include CHIRALCEL OB (registered trade name), CHIRALCEL OD (registered trade name), CROWNPAK CR(+) (registered trade name), CHIRALCEL CA-1 (registered Trade name), CHIRALCEL OA (registered trade name), CHIRALCEL OB (registered trade name), CHIRALCEL OK (registered Trade name), CHIRALCEL OJ (registered trade name), CHIRALCEL OC (registered trade name), CHIRALCEL OF (registered trade name), CHIRALCEL OG (registered trade name), CHIRALPAK WH (registered trade name), CHIRALPAK WM (registered trade name), CHIRALPAK WE (registered trade name), CHIRALPAK OT(+) (registered trade name), CHIRALPAK OP(+) (registered trade name), CHIRALPAK AS (registered trade name) and CHIRALPAK AD (registered trade name) all of which are products of Daicel Chemical Industries, Ltd.

Particle Diameter of Packing

Although the average particle diameter of the packing varies depending on the kind of the optical isomers to be resolved, the volume flow rate of the solvent flowing in the simulated moving bed, etc., it is usually 1 to 100 µm, preferably 5 to 75 µm. In order to keep the pressure drop in the simulated moving bed-on a low level, it is desirable to regulate the average particle diameter of the packing to 15 to 75 µm. When the average particle diameter of the packing is within the above-described range, the pressure drop in the simulated moving bed can be reduced to, for example, 10 kgf/cm$^2$ or below. On the contrary, as the average particle diameter of the packing increases, The number of the theoretical adsorption plates decreases. Therefore when only the number of the practical theoretical adsorption plates is to be attained, the average particle diameter of the above-described packing is usually 1 to 50 µm.

Eluent

The eluents to be fed through the inlet for an eluent include, for example, organic solvents such as alcohols, e.g. methanol, ethanol and isopropanol, hydrocarbons, e.g. hexane, and aqueous salt solutions such as aqueous copper sulfate solution and aqueous perchlorate solution. The eluent is suitably selected depending on the kind of the compounds to be optically resolved.

Optical Isomer to be Optically Resolved

The optical isomer mixture to be fed through an inlet for a liquid containing an optical isomer mixture is not particularly limited. The optical isomer mixture may comprise various compounds used in the fields of medicines, agricultural chemicals, foods, feeds, flavors, etc., such as thalidomide (a medicine), EPN (an organophosphorus agricultural chemical), monosodium glutamate (a chemical seasoning) and menthol (a flavor), and also optically active alcohols and optically active esters. The invention can also successfully treat dihydropyridine compounds, oligopeptides, arylalkylamine compounds, pyridylphenylmethane compounds, benzenesulfonic amide compounds, 2-allylpropionic acid, sulfoxide compounds, pyridone-carboxylic acids, arylacetic acids, beta-lactam compounds, tetrahydroquinolines and benzodiazepine compounds.

Steps in the Simulated Moving Bed System

The separation of optical isomers by adsorption with the simulated moving bed system of the present invention is conducted by the continuous circulation of the basic steps including those of adsorption, concentration, desorption and recovery of the eluent, which will be described below.

(1) Adsorption step:

When an optical isomer mixture is brought into contact with packings, an optical isomer (strongly adsorbable component) easily adsorbable on the packing is adsorbed and the other optical isomer (weakly adsorbable component) difficultly adsorbable on the packing is recovered as the raffinate together with the eluent.

(2) Concentration step:

The packing having the strongly adsorbable component adsorbed thereon is brought into contact with a part-of an extract which will be described below to expel the weakly adsorbable component remaining on the packing, thereby concentrating the strongly adsorbable component.

(3) Desorption step:

The packing containing the strongly adsorbable component thus concentrated is then brought into contact with the eluent to expel this component from the packing to discharge it as the extract together with the eluent from the simulated moving bed.

(4) Eluent-recovering step:

The packing on which substantially only the eluent is adsorbed is then brought into contact with a part of the raffinate, whereby a part of the eluent contained in the packing is recovered as an eluent recovery.

The present invention which will be described in more detail with reference to the attached drawings is as follows.

In FIG. 1, numerals 1 to 12 refer unit packed beds containing packings, and they are connected to each other through a liquid passage. Numeral 13 refers to an eluent-feeding line, 14 to an extract ejecting line, 15 to a line for feeding a liquid containing an optical isomer mixture, 18 to a raffinate ejecting line, 17 to a recycle line and 18 to a circulation pump.

In the arrangement of the unit packed beds 1 to 12 and lines 13 to 18 shown in FIG. 1, the unit packed beds 1 to 3 take part in the desorption step, The unit packed beds 4 to 8 in the concentration step, the unit packed beds 7 to 9 in the adsorption step, and the unit packed beds 10 to 12 in the eluent-recovering step.

In This simulated-moving bed, the eluent-feeding line, the line for feeding a liquid containing an optical isomer mixture and the respective ejecting lines are moved at a distance corresponding to one unit packed bed in the direction of solvent flow by, for example, operating valves at predetermined time intervals.

Accordingly, in the second stage, the unit packed beds 2 to 4 take part in the desorption step, the unit packed beds 5 to 7 in the concentration step, the unit packed ones 8 to 10 in the adsorption step and the unit packed ones 11 to 1 in the eluent-recovering step. By successively conducting such an operation, the respective steps move at a distance corresponding to one unit packed bed, and the separation treatment of the optical isomer mixture is conducted continuously and efficiently.

The extract thus ejected with the simulated moving bed system comprises an optical isomer having an optical purity of as high as at least 90%, for example, at least 95% or even at least 98%, contained in the solvent, and the raffinate comprises the other optical-isomer having an optical purity of as high as that described above in the solvent.

Another Embodiment of the Simulated Moving Bed

Figure 2:
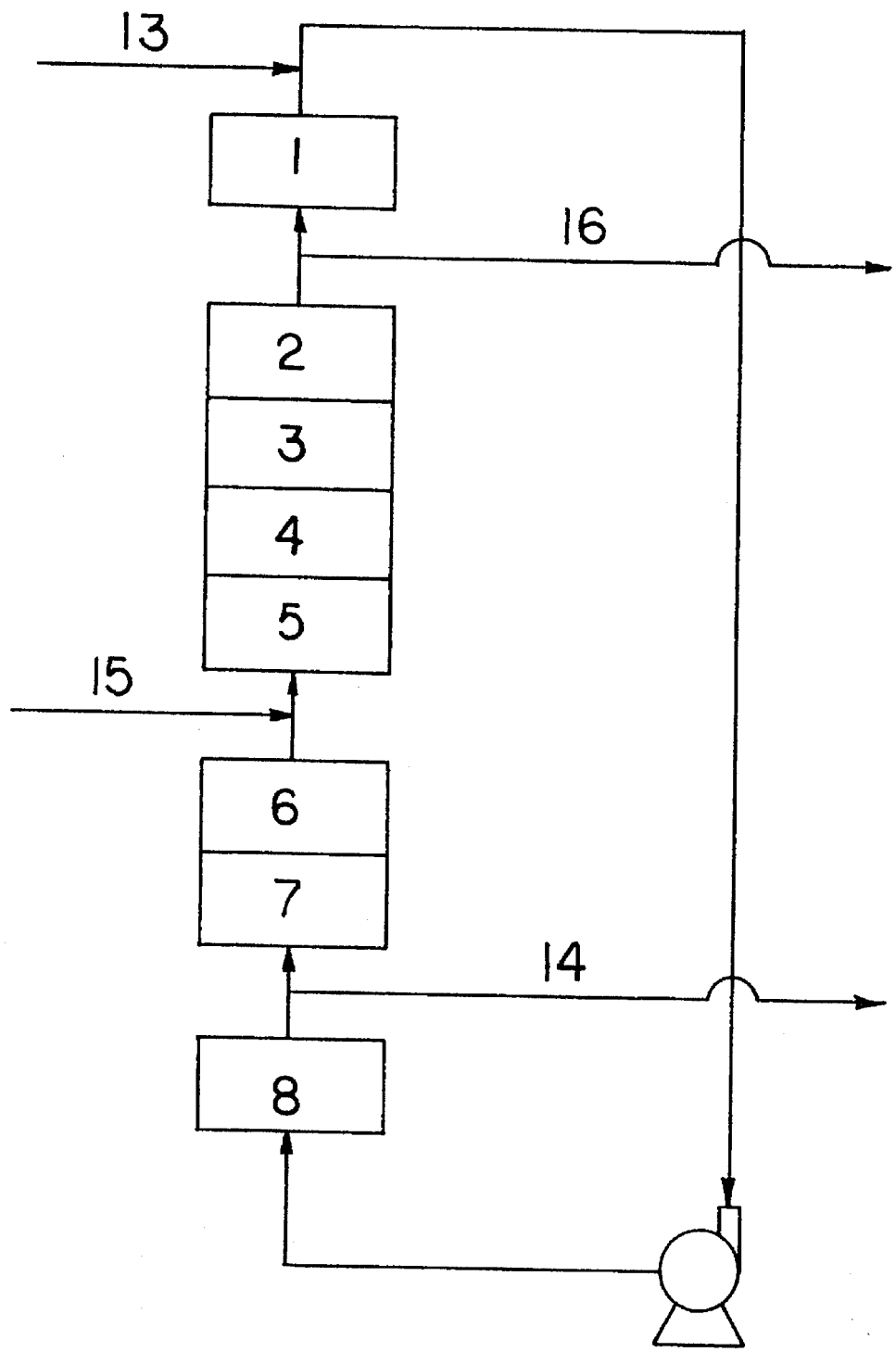
FIG. 2 is a drawing for illustrating another example of the apparatuses usable for conducting the process of the present invention.

The simulated moving bed to be used in the process of the present invention is not limited to that shown in FIG. 1 but another simulated moving bed shown in FIG. 2 is also usable.

In the arrangement of unit packed beds 1 to 8 and lines 13 to 16 shown in FIG. 2, the unit packed bed 1 takes part in the elution and recovering steps, the unit packed beds 2 to 5 in the adsorption step, the unit packed beds 8 and 7 in the concentration step, and the unit packed bed 8 in the desorption step.

In such a simulated moving bed, the liquid-feeding lines and ejecting lines are moved at a distance corresponding to one unit packed bed in the direction of liquid flow by, for example, operating valves at predetermined time intervals. Accordingly, in the next arrangement of the unit packed beds, the unit packed bed 2 takes part in eluent-feeding step, the unit packed beds 3 to 6 in the adsorption step, the unit packed beds 7 and 8 in the concentration step, and the unit packed bed 1 in the desorption step. By successively conducting such an operation, the separation treatment of the optical isomer mixture is conducted continuously and efficiently.

B. Recovery of the solvent:

In the present invention, one or both of the extract and raffinate obtained according to the above-described simulated moving bed system are sent to the solvent-recovering step.

The recovery of the solvent and separation of the optical isomers from the extract and/or raffinate can be conducted in an evaporator and/or a still. The evaporator and the still are preferably of reduced pressure type. The evaporator of reduced pressure type is preferred, since the optical isomers can be separated without denaturalizing them by heating, since oxidation can be prevented and the evaporation temperature can be lowered.

The evaporators usable herein are preferably film evaporators such as a forced film evaporator, ascending film evaporator, falling film evaporator, or stirred liquid film evaporator. These evaporators are usable either singly or in combination of two or more evaporators of the same or different types. The stills are preferably molecular stills such as a batchwise molecular still, falling film molecular still or centrifugal film molecular still. These molecular stills of reduced pressure type are usable either singly or in combination of two or more stills of the same or different types.

In the process of the present invention, it is preferred that the extract and/or raffinate ejected from the simulated moving bed is separated in a separator comprising a combination of two or three kinds of falling film evaporator and forced film evaporator, since the use of the combination of the two or three apparatuses can reduce the residence time in these apparatuses, thereby preventing the racemization advantageously. A combination of two or more apparatuses of the same kind arranged in series or a combination of them with the molecular still is also desirable.

Specifically, as shown in FIG. 1, the extract is concentrated to about 30 to 50% in the first falling film evaporator 19, then to about 40 to 70% in the second falling film evaporator 20, and further to about 60 to 99% in a forced film evaporator 21.

The solvent recovered with the evaporator is usually stored in a recovery tank temporarily. In FIG. 1, numeral 22 refers to a recovery tank for temporarily storing recovered solvent. The concentrate containing an optical isomer obtained by the concentration with the evaporator is temporarily stored in a reservoir. Numeral 23 in FIG. 1 refers to the reservoir. When the optical isomer mixture is in the form of a powder, the extract is concentrated in a concentrator, such as the above shown evaporator and other known concentrators, such that an optical isomer does not precipitate and then formed into a powder with a powder-forming device such as a granulator, a drier and a rotary evaporator.

On the other hand, the raffinate contains another optical isomer, which is an antipode of the optical isomer contained in the extract, and the solvent. The recovery of the solvent from the raffinate can be conducted in the same manner as that of the recovery of the solvent from the extract.

C. Reuse of the solvent:

In the process of the present invention, the solvent recovered as described above is recycled for use as the eluent or reused for the preparation of a liquid containing an optical isomer mixture. In such a case, the purity of the solvent to be reused is at least 98%. For obtaining such a purity, the use of a still is preferable. The solvent recovered above, in the invention, can be used as a waste liquid or a preparation for an optical isomer mixture. It is not desirable, however, that the recovered solvent contains optical isomers, which will influence a raffinate and an extract in the simulated moving bed system. For this reason, the recovered solvent is preferably purified. The solvent being suitable for re-use has a purity of 98 percent or more. A recovered solvent not containing an optical isomer can be re-used, without purification, such as distillation, as far as it satisfies the requirements which the solvent must have before being first used. A mixture of solvents can be used as long as they do not substantially differ from each other in view of contaminants contained therein. The purity of the recovered solvent has an influence on the quality of separated optical isomers. Accordingly, it is required to determine in advance the requirements of a recovered solvent, taking into account the effects from the simulated moving bed system. In FIG. 1, the concentration of the solvent stored in the recovery tank 22 is increased to a necessary purity in a still 25. When the above purity can be kept, the separation of the optical isomers can be efficiently conducted by the simulated moving bed system. The still 25 is a distillation column, preferably including a reservoir for the purified solvent, which is well known in the chemical industry. The recovering distillation can be conducted batch-wise or continuously. It can also be effected in a distillation column such as a packed column and a plate column with one or more ideal plates in the batch-wise system or with five or more plates in the continuous method.

D. Reuse of the optical isomers:

In the process of the present invention, it is also preferred to convert an optical isomer which is not an intended antipode contained in the extract or raffinate into the racemic modification by heating and Then to return the solvent containing the racemic modification into the line for feeding a liquid containing an optical isomer mixture after, if necessary, adjusting the concentration of the liquid. In this case, the extract or raffinate can be directly racemized, or the racemization can be conducted by treating a solution containing an optical isomer obtained after recovering the solvent from the extract or raffinate, or the racemic modification thus obtained can be dissolved in a fresh solvent to obtain a solution containing the racemic modification. The racemization of the optical isomer can be conducted by heating or by using an enzyme. In either case, well-known racemization methods can be suitably selected. Irrespective of the employed racemization method, the racemization conditions are suitably determined depending on the kind of the optical isomer.

In FIG. 1, the raffinate is heated in a racemization tank 24 and the solvent containing the racemic modification thus obtained is returned into a line 15 for feeding a liquid containing an optical isomer mixture.

By thus separating a desired optical isomer as, for example, the extract and, on the other hand, heating the raffinate containing an undesired optical isomer to form a racemic modification to be reused, an intended optical isomer can be separated further efficiently. Although the intended optical isomer is contained in the extract in the above description of the present invention given with reference to the drawings, the intended optical isomer may be contained in the raffinate in another case. In the latter case, the term "extract" in the above description referring to the extract is to be replaced by "raffinate", so that the matter can be easily understood.

According to the present invention, an optical isomer mixture can be continuously and efficiently separated and the solvent can be recovered after the use. Since the recovered solvent can be reused as the solvent circulating through the simulated moving bed, the solvent is not wasted and the amount of the eluent used is small, so that a closed system having a high efficiency with respect to solvent can be obtained. Further, the adsorption efficiency is improved by regulating the average particle diameter of the packing for optical resolution to be packed in the simulated moving bed to 1 to 100 μm. In addition, by racemizing the optical isomer which is an antipode contained in the raffinate or extract separated in the simulated moving bed system, the raffinate or extract can convert a solution containing a racemic modification. And since the solution is reused as a liquid containing an optical isomer mixture to be fed, the intended optical isomer can be separated in a high yield.

EXAMPLES

The following Examples will further illustrate the present invention, which by no means limit the present invention.

EXAMPLE 1

A simulated moving bed apparatus shown in FIG. 1, which was prepared by connecting twelve columns having an inner diameter of 2 cm and a length of 50 cm as the unit packed beds to each other and filling them with packings for optical isomer resolution (CHIRALCEL OB having a particle diameter of 20 μm; a product of Daicel Chemical Industries, Ltd.), was used. In this simulated moving bed apparatus were arranged the columns so that every three unit packed beds took part in the adsorption step, concentration step, desorption step and eluent-recovering step. 6 ml/min of 1,3-butanediol diacetate (total isomer concentration: 1,000 mg/ml) was fed as a liquid containing an optical isomer mixture. 27.9 ml/min of a liquid mixture of hexane and isopropanol (volume ratio: 9/1) was fed as the eluent. The solvent circulating the solvent circulation passage was the same as the eluent.

26.6 ml/min of an extract containing a strongly adsorbable optical isomer (concentration: 105.7 mg/ml: optical purity: 98% e.e.) was obtained through the outlet for the extract of the simulated moving bed apparatus.

On the other hand, 7.3 ml/min of a raffinate containing a weakly adsorbable, other optical isomer (concentration: 411.4 mg/ml; optical purity: 98% e.e.) was obtained through the outlet for the raffinate of the simulated moving bed apparatus.

The extract obtained as described above was fed into the first falling film evaporator at 70° C. under atmospheric pressure. The concentrate obtained in this evaporator was fed into the second falling film evaporator at 43° C. under 50 Torr and then the concentrate obtained in this second evaporator was fed into a forced film evaporator at 10° C. under 50 Torr to give a concentrate containing the strongly adsorbable optical isomer in a concentration of at least 98% from the forced film evaporator. The solvent recovered from the respective evaporators was stored in the reservoir.

On the other hand, the raffinate obtained as described above was heated at 90° C. for 5 hours to give a solution containing a racemic modification.

The solvent stored in the reservoir was reused as the circulating solvent in the simulated moving bed apparatus, and the solution containing the racemic modification in the heating tank was returned into the line for feeding a liquid containing an optical isomer mixture.

By the above process, the strongly adsorbable optical isomer having an optical purity of 98% e.e. could be obtained in an amount of at least 83% based on the racemic modification fed into this system.

COMPARATIVE EXAMPLE 1

The separation was conducted batchwise by using the same packing and the same starting material as those in Example 1 and a single column to compare the throughput and the utilization rate of the eluent. The results are given in Table 1.

TABLE 1

| | Simulated moving bed process | Batchwise process |
|---|---|---|
| Throughput per unit packing per unit time (mg/ml-bed · min) | 2.4 | 0.084 |
| Utilization rate of eluent (mg/ml-feed) | 0.0093 | 2.0 |

It is apparent from this Table 1 that the employment of the simulated moving bed process is superior to that of the batchwise process in the throughput and the utilization rate of the eluent.

EXAMPLE 2

The same apparatuses as those of Example 1 were used except that columns having an inner diameter of 3 cm and a length of 100 cm were used as the unit packed column and CHIRALCEL OB having an average particle diameter of 30 to 50 μm was used as the packing. 6 ml/min of α-phenylethyl alchol (total isomer concentration: 1,000 mg/ml) was fed. 61.4 ml/min of a liquid mixture of hexane and isopropanol (volume ratio: 9/1) was fed as the eluent. The solvent circulating the solvent circulation passage was the same as the eluent.

58.5 ml/min of an extract containing a strongly adsorbable optical isomer (concentration: 28.6 mg/ml; optical purity: 98% e.e.)was obtained through the outlet for the extract of the simulated moving bed apparatus.

On the other hand, 8.9 ml/min of a raffinate containing a weakly adsorbable, other optical isomer (concentration: 336 mg/ml; optical purity: 98% e.e.) was obtained through the outlet for the raffinate of the simulated moving bed apparatus.

The extract obtained as described above was treated in the same manner as that of Example 1 to give a concentrate containing the strongly adsorbable optical isomer in a concentration of at least 98% by weight. The solvent recovered from the evaporator and the molecular still was stored in the reservoir.

The solvent stored in the reservoir was reused as the circulating solvent in the simulated moving bed apparatus, and the raffinate was treated in the same manner as that of Example 1. The resultant solution containing a racemic modification was returned into the line for feeding a liquid containing an optical isomer mixture.

COMPARATIVE EXAMPLE 2

The separation was conducted batchwise by using the same packing and the same starting material as those of Example 2 and a single column to compare the throughput and the utilization rate of the eluent. The results are given in Table 2.

TABLE 2

| | Simulated moving bed process | Batchwise process |
|---|---|---|
| Throughput per unit packing per unit time (mg/ml-bed · min) | 0.53 | 0.014 |
| Utilization rate of eluent (mg/ml-feed) | 0.02 | 4.5 |

EXAMPLE 3

A simulated moving bed apparatus shown in FIG. 2, which was prepared by connecting eight columns having an inner diameter of 2 cm and a length of 15 cm as the unit packed beds to each other and filling them with packings for optical isomer resolution (CHIRALCEL OB having a particle diameter of 45 μm; a product of Daicel Chemical Industries, Ltd.) was used. 5.9 ml/min of a mixed solution containing 4,200 ppm of racemic modification of α-phenylethyl alcohol was fed as a liquid containing an optical isomer mixture in the simulated moving bed apparatus. 24.2 ml/min of a liquid mixture of hexane and isopropanol (volume ratio: 90/10) was fed as the eluent. The solvent circulating the solvent circulation passage was the same as the eluent. The liquid-feeding lines and ejecting lines were moved at a distance corresponding to one unit packed bed in the direction of liquid flow by automatically switching an eight-way rotary valve at intervals of 3 min to continuously conduct the treatment at 28° C. in a certain period of time.

20.2 ml/min of an extract containing a strongly adsorbable optical isomer [(R)-(+)-α-phenylethyl alcohol] (concentration: 613.4 ppm; optical purity: at least 99.9% e.e.) was obtained through the outlet for the extract of the simulated moving bed apparatus.

On the other hand, 9.7 ml/min of a raffinate containing a weakly adsorbable, other optical isomer (concentration: 1,251.5 ppm; optical purity: at least 99.9% e.e.) was obtained through the outlet for the raffinate of the simulated moving bed apparatus.

The pressure drop in this simulated moving bed apparatus was 7.9 kg/cm$^2$.

The extract obtained as described above was fed into the same solvent recovering apparatuses as those of Example 1 to give a concentrate containing the strongly adsorbable optical isomer in a concentration of 98% by weight and the solvent having a purity of at least 99% by weight. The recovered solvent was stored in the reservoir.

The solvent stored in the reservoir was reused in the fluid passage in the simulated moving bed apparatus, and the raffinate was converted into a solution containing a racemic modification by heating and returned into the line for feeding a liquid containing an optical isomer mixture.

We claim:

1. A process for separating optical isomers from a mixture containing the same comprising the steps of: introducing a liquid containing an optical isomer mixture and an eluent into a packed bed column containing packings for optical resolution, said column having its ends connected to each other through a fluid passage so that liquid may be circulated therethrough in endless, one-way flow relationship, an inlet for the eluent, an outlet for a liquid extract containing a strongly adsorbable isomer, an inlet for the liquid containing the optical isomer mixture and an outlet for a liquid raffinate containing a weakly adsorbable optical isomer arranged in that order in the liquid flow direction along the packed bed column; circulating said liquid containing the optical isomer mixture and eluent in one-way flow through the column; simultaneously removing a liquid containing one optical isomer and a liquid containing another optical isomer from the column; intermittently and successively moving the inlets and outlets in the direction of liquid flow along the column; and maintaining a pressure drop of no higher than 10 kgf/cm$^2$ through the packed bed column, the packing in said packed bed having an average particle size of from 1 to 100 μm.

2. The process of claim 1, wherein the recovered solvent is reused in the process.

3. The process for recovering optical isomers and a solvent in optical resolution according to claim 1, wherein the solvent is separated from the extract and/or raffinate obtained with the simulated moving bed system with an evaporator and/or a still.

4. The process for recovering optical isomers and a solvent in optical resolution according to claim 3, wherein the evaporator and/or still is of reduced pressure type.

5. A process for using a solvent by circulation, characterized by returning the solvent recovered by the process according to claim 1 into the fluid passage.

6. The process for using a solvent by circulation according to claim 5, wherein the recovered solvent has a purity of at least 98%.

7. A process for reusing an optical isomer, wherein the optical isomer as an antipode in the extract or raffinate set forth in claim 1 is racemized and the resultant liquid containing an optical isomer mixture is returned into the inlet for a liquid containing an optical isomer mixture.

8. A process for separating optical isomers from a mixture containing the same comprising the steps of: introducing a liquid containing an optical isomer mixture and an eluent into a packed bed column containing packings for optical resolution, said column having its ends connected to each other through a fluid passage so that liquid may be circulated therethrough in endless, one-way flow relationship, an inlet for the eluent, an outlet for a liquid extract containing a strongly adsorbable isomer, an inlet for the liquid containing the optical isomer mixture and an outlet for a liquid raffinate containing a weakly adsorbable optical isomer arranged in that order in the liquid flow direction along the packed bed column; circulating said liquid containing the optical isomer mixture and eluent in one-way flow through the column; simultaneously removing a liquid containing one optical isomer and a liquid containing another optical isomer from the column; intermittently and successively moving the inlets and outlets in the direction of liquid flow along the column; said optical isomer mixture being compounds used as at least one of medicines, agricultural chemicals, foods, feeds and flavors.

9. The process of claim 8, wherein said optical isomer mixture is at least one member selected from the group consisting of optically active alcohols and optically active esters.

10. The process of claim 8, wherein said optical isomer mixture is at least one member selected from the group consisting of dihydropyridine compounds, oligopeptides, arylalkylamine compounds, pyridylphenylmethane compounds, benzenesulfonic amide compounds, 2-allylpropionic acid, sulfoxide compounds, pyridonecarboxylic acids, arylacetic acids, beta-lactam compounds, tetrahydroquinolines and benzodiazepine compounds.

11. The process of claim 8, wherein the recovered solvent is reused in the process.

12. A process for separating optical isomers from a mixture containing the same comprising the steps of: introducing a liquid containing an optical isomer mixture and an eluent into a packed bed column containing packings for optical resolution, said column having its ends connected to each other through a fluid passage so that liquid may be circulated therethrough in endless, one-way flow relationship, an inlet for the eluent, an outlet for a liquid extract containing a strongly adsorbable isomer, an inlet for the liquid containing the optical isomer mixture and an outlet for a liquid raffinate containing a weakly adsorbable optical isomer arranged in that order in the liquid flow direction along the packed bed column; circulating said liquid containing the optical isomer mixture and eluent in one-way flow through the column; simultaneously removing a liquid containing one optical isomer and a liquid containing another optical isomer from the column; recovering the solvent from the extract and/or raffinate separated from the column; intermittently and successively moving the inlets and outlets in the direction of liquid flow along the column; purifying the recovered solvent to a purity of at least 98%; and reusing the purified solvent in the process.

* * * * *

UNITED STATES PATENT AND TRADEMARK OFFICE
CERTIFICATE OF CORRECTION

PATENT NO. : 5,498,752
DATED : March 12, 1996
INVENTOR(S) : Masakazu Negawa et al It is certified that error appears in the above-indentified patent and that said Letters Patent is hereby corrected as shown below:

On the title page: Item

[30]   PCT Filed:        Aug. 10, 1992
[86]   PCT No.:          PCT/JP92/01024

Signed and Sealed this

Seventeenth Day of September, 1996

Attest:

BRUCE LEHMAN

Attesting Officer        Commissioner of Patents and Trademarks